United States Patent
Lacoste et al.

(10) Patent No.: US 7,410,765 B2
(45) Date of Patent: Aug. 12, 2008

(54) SYSTEM FOR PROTEASE MEDIATED PROTEIN EXPRESSION

(75) Inventors: Arnaud Lacoste, Los Angeles, CA (US); Christopher J. Evans, Malibu, CA (US)

(73) Assignee: The Regents of the University of California, Oakland, CA (US)

( * ) Notice: Subject to any disclaimer, the term of this patent is extended or adjusted under 35 U.S.C. 154(b) by 68 days.

(21) Appl. No.: 11/281,644

(22) Filed: Nov. 17, 2005

(65) Prior Publication Data

US 2006/0105953 A1 May 18, 2006

Related U.S. Application Data

(60) Provisional application No. 60/628,694, filed on Nov. 17, 2004.

(51) Int. Cl.
*C12Q 1/68* (2006.01)
*C12N 15/00* (2006.01)
*C12N 1/20* (2006.01)
*C07H 21/02* (2006.01)

(52) U.S. Cl. .............. 435/6; 435/252.3; 435/320.1; 435/69.1; 536/23.1

(58) Field of Classification Search ............ 536/23.1; 435/69.1, 252.3, 320.1, 6
See application file for complete search history.

(56) References Cited

FOREIGN PATENT DOCUMENTS

WO 96/36698 * 11/1996

OTHER PUBLICATIONS

Mildner et al., Protein Expression and Purification, 16, 347-354, 1999.*
Bark, SJ, et al., "Fluorescent indicators of peptide cleavage in the trafficking compartments of living cells: peptides . . . dyes", Methods 20(4):429-35 (Apr. 2000).
Bevis, B. et al., "Rapidly maturing variants of the Discosoma red fluorescent protein (DSRed)", Nat. Biotechnology, 20:83-87 (2002).
Dantuma, N., et al., "Short-lived green fluorescent proteins for quantifying ubiquitin/proteasome-dependent . . . cells", Nature Biotechnology, 18:538-543 (2000).
Felber, L. et al., Evaluation of the CFP-substrate-YFP system for protease studies:advantages and limitations, Biotechniques 36(5)878-85 (May 2004).
Johnson, E. et al., "A proteolytic pathway that recognizes ubiquitin as a degradation signal", J of Biological Chemistry, 270(29):17442-17456 (Jul. 1995).
Lazebnik, Y. A. et al., "Cleavage of poly(ADP-ribose) polymerase by a proteinase with properties like ICE", Letters to Nature, 371:346-347, (1994).
Lindsten, K. et al., "A transgeneic mouse model of the ubiquitin/proteasome system", Nat Biotechnology, 21(8):897902 (2003).
Yabun, T. et al., "Characterization of zebrafish caspase-3 and induction of apoptosis through ceramide generation in fish fathead..embryo", Biochem J. 360:39-37 (2001) GB.

* cited by examiner

*Primary Examiner*—Maryam Monshipouri
(74) *Attorney, Agent, or Firm*—Candy + Lortz LLP; Karen S. Canady (57) ABSTRACT

The present invention provides methods and materials that can be used to detect, examine and exploit protease mediated protein expression. An illustrative embodiment of the invention is a polynucleotide encoding a polypeptide having a plurality of operatively linked elements comprising a polypeptide degradation signal that functions as a proteosome substrate; a polypeptide of interest having an observable activity; and a linker disposed between the polypeptide degradation signal and the polypeptide of interest. The linker comprises a protease recognition motif that is capable of being specifically recognized and cleaved by a protease. The activity of the polypeptide of interest is observed when the motif is specifically recognized and cleaved by the protease; and the activity of the polypeptide of interest is decreased or not observed when the motif is not specifically recognized and cleaved by the protease.

9 Claims, 7 Drawing Sheets

In the absence of protease activity:

In the presence of protease activity:

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
```

```
<223> OTHER INFORMATION: synthetic protease recognition motif

<400> SEQUENCE: 1

Asp Glu Val Asp
 1

<210> SEQ ID NO 2
<211> LENGTH: 16
<212> TYPE: PRT
<213> ORGANISM: Artificial Sequence
<220> FEATURE:
<223> OTHER INFORMATION: synthetic peptide linker

<400> SEQUENCE: 2

Gly Asp Glu Val Asp Gly Asp Glu Val Asp Gly Asp Glu Val Asp Gly
 1               5                  10                  15

<210> SEQ ID NO 3
<211> LENGTH: 31
<212> TYPE: DNA
<213> ORGANISM: Artificial Sequence
<220> FEATURE:
<223> OTHER INFORMATION: synthetic primer

<400> SEQUENCE: 3
atacgaattc atgcagatct tcgtcaagac c                              31

<210> SEQ ID NO 4
<211> LENGTH: 50
<212> TYPE: DNA
<213> ORGANISM: Artificial Sequence
<220> FEATURE:
<223> OTHER INFORMATION: synthetic primer

<400> SEQUENCE: 4
gcgggatcct gtcgaccaag cttccccacc actcccctga gacgcagcac           50

<210> SEQ ID NO 5
<211> LENGTH: 80
<212> TYPE: DNA
<213> ORGANISM: Artificial Sequence
<220> FEATURE:
<223> OTHER INFORMATION: synthetic primer

<400> SEQUENCE: 5
gacaggatcc aggtgacgag gtcgacaagg gtgacgaggt cgacggtgac gaggtcgacg  60
gtatggcctc ctccgagacg                                            80

<210> SEQ ID NO 6
<211> LENGTH: 30
<212> TYPE: DNA
<213> ORGANISM: Artificial Sequence
<220> FEATURE:
<223> OTHER INFORMATION: synthetic primer

<400> SEQUENCE: 6
gagtcgcggc cgctacagga acaggtggtg                                 30

<210> SEQ ID NO 7
<211> LENGTH: 35
<212> TYPE: DNA
<213> ORGANISM: Artificial Sequence
<220> FEATURE:
<223> OTHER INFORMATION: synthetic primer

<400> SEQUENCE: 7
```

```
actagtcgac attaatagta atcaattacg gggtc                                  35

<210> SEQ ID NO 8
<211> LENGTH: 72
<212> TYPE: DNA
<213> ORGANISM: Artificial Sequence
<220> FEATURE:
<223> OTHER INFORMATION: synthetic primer

<400> SEQUENCE: 8
atcagtcgac tgccatttca ttacctcttt ctccgcaccc gacatagata cgccttaaga      60
tacattgatg ag                                                           72

<210> SEQ ID NO 9
<211> LENGTH: 25
<212> TYPE: DNA
<213> ORGANISM: Artificial Sequence
<220> FEATURE:
<223> OTHER INFORMATION: synthetic primer

<400> SEQUENCE: 9
ttatggttca ttcttcgccg tttcg                                             25

<210> SEQ ID NO 10
<211> LENGTH: 25
<212> TYPE: DNA
<213> ORGANISM: Artificial Sequence
<220> FEATURE:
<223> OTHER INFORMATION: synthetic primer

<400> SEQUENCE: 10
cctcttacct cagttacaat ttata                                             25
```

SYSTEM FOR PROTEASE MEDIATED PROTEIN EXPRESSION

This application claims the benefit of U.S. provisional patent application No. 60/628,694, filed Nov. 17, 2004, the entire contents of which are incorporated herein by reference.

FIELD OF THE INVENTION

The present invention provides methods and materials that can be used to detect and exploit protease mediated protein expression.

BACKGROUND OF THE INVENTION

Proteases or enzymes with proteolytic activity catalyze the cleavage of peptide bonds. Proteolytic reactions are fundamental to many key biological processes such as cell growth, cell death, blood clotting, matrix remodeling and immune defense. A large number of pathogens, including viruses, bacteria and multicellular parasites also use proteases to infect host cells, complete their life cycle and degrade the host immune system. Therefore, a large number of specific proteases are becoming attractive drug targets. For example, protease inhibitors are being developed for the effective management of AIDS (e.g. HIV-1 protease inhibitors such as Ritonavir, Nelfinavir or Saquinavir), HCV hepatitis (hepatitis C virus protease inhibitors), malaria, Chagas' disease and schistosomiasis (papain, plasmepsin and falcipain inhibitors). Protease inhibitors are also being tested for the treatment of hypertension (angiotensin-converting enzyme inhibitors), liver cirrhosis (caspase-8 inhibitors), Alzheimer's disease (beta site APP-cleaving enzyme inhibitors), autoimmune diseases (cathepsin S inhibitors), rheumatoid- or osteoarthritis and cancer (matrix metalloproteinase—MMP- and caspase-1 inhibitors) (see, e.g. Vandeputte-Rutten et al., (2002) Curr Opin Struct Biol. 12:704-708; and Docherty et al., (2003) Biochem Soc Symp. 70:147-161).

In the past two decades, almost 250,000 scientific articles reported research on proteases, indicating that research in this field is very dynamic. Recent success with HIV-1 protease inhibitors and other anti-protease drugs used to treat cancer or autoimmune diseases proved that proteolytic activities are attractive drug targets for modern medical therapy. Advances in genomic research provide an increasing number of potential ways to modulate protease activities and progress in bioinformatics now enable drug-discovery researchers to read and analyze large amounts of data in record time. The bottleneck for high-throughput drug screening is now at the level of bioassays. Many compounds initially identified using in vitro assays fail in later phases of drug development because they cannot be used in a biologically relevant environment.

An illustrative cellular process of interest that involves specific proteolytic reactions is apoptosis or programmed cell death. Programmed cell death (PCD) is a fundamental process for normal embryonic development and maintenance of adult tissue homeostasis (see, e.g. Metzstein et al. *Trends Genet.* 14, 410-416 (1998); Putcha et al. *Cell Death Differ.* 11, 38-48 (2004); and Danial et al. *Cell* 116, 205-219 (2004)). Studies in invertebrates such as *C. elegans* have provided important clues about the molecular mechanisms of PCD1. However vertebrate models allowing genetic screens and in vivo studies would facilitate research in this field because fundamental differences exist between invertebrate and vertebrate PCD pathways (see, e.g. Putcha et al. *Cell Death Differ.* 11, 38-48 (2004); and Danial et al. *Cell* 116, 205-219 (2004)).

Zebrafish is one promising vertebrate model to study PCD because it presents several features which made *C. elegans* a successful model in this field of research, including a rapid development, a transparent embryo and amenability to large-scale genetic screens (see, e.g. Haffter, P., et al. *Development.* 123, 1-36; and Driever, W. et al. *Development* 123, 37-46 (1996)). Higher gene conservation between teleosts and human is an advantage of zebrafish over *C. elegans* but the nematode is a relatively less complex organism exhibiting an invariant pattern of PCD which can be easily observed in vivo (see, e.g. Metzstein et al. *Trends Genet.* 14, 410-416 (1998)). In zebrafish, only terminal deoxynucleotide transferase-mediated dUTP nick-end labelling (TUNEL) on fixed preparations has revealed normal patterns of apoptosis so far (see, e.g. Cole et al. *Dev. Biol* 240, 123-142 (2001)).

There is a need in the art to understand and characterize the physiology of proteolytic processes such as those involved in programmed cell death. This need has increased markedly in recent years as artisans seek efficient bioassays that can, for example, determine the role of proteases in both normal cellular processes as well as in the context of specific diseases. Also needed are improved methods for targeted delivery of therapeutic agents to cells. The invention disclosed herein satisfies these and other needs.

SUMMARY OF THE INVENTION

The present invention provides methods and materials that can be used to detect, examine and exploit protease mediated protein expression. An illustrative embodiment of the invention is a polynucleotide (preferably one that is present on a vector, such as a plasmid) encoding a protease-regulated polypeptide having a plurality of operatively linked elements comprising a protein degradation signal that functions as a proteasome substrate; a polypeptide of interest having an observable activity; and a linker disposed between the protein degradation signal and the polypeptide of interest.

In this embodiment, the linker comprises a protease recognition motif that is capable of being specifically recognized and cleaved by a protease. In the presence of the protease, the protein degradation signal is cleaved from the polypeptide of interest so that the polypeptide of interest is not susceptible to proteasomal degradation. In the absence of the protease, the protein degradation signal remains operatively linked to the polypeptide of interest so that the polypeptide of interest is susceptible to proteasomal degradation. The activity of the polypeptide of interest is thereby observed when the protease recognition motif is specifically recognized and cleaved by the protease; and the activity of the polypeptide of interest is decreased or not observed when the protease recognition motif is not specifically recognized and cleaved by the protease.

The invention further provides a protease-regulated polypeptide having this plurality of operatively linked elements. The invention also provides a method of testing an environment for the presence of a protease comprising placing this protease-regulated polypeptide in the environment and observing the presence or absence of the observable activity of the polypeptide of interest, wherein the presence of the observable activity is indicative of the presence of the protease. Another embodiment of the invention is a method of examining the ability of a compound to modulate the activity of a protease comprising exposing the protease-regulated polypeptide to the protease and observing the presence or absence of the observable activity of the polypeptide of interest; and then comparing the activity so observed to the activity of the polypeptide of interest that is observed when the protease-regulated polypeptide is exposed to the protease in combination with the compound to be examined so that the compound's ability to modulate the activity of the protease is examined.

Yet another embodiment of the invention is a method of delivering a polypeptide of interest to a cell having a known protease activity. The method comprises placing the protease-regulated polypeptide within a cell having the known protease activity. The linker in the polypeptide comprises a protease recognition motif that is specifically recognized and cleaved by the known protease activity so that the polypeptide of interest is delivered to the cell. Optionally, the polypeptide of interest is a reporter protein and/or a therapeutically active polypeptide.

Figure 6:
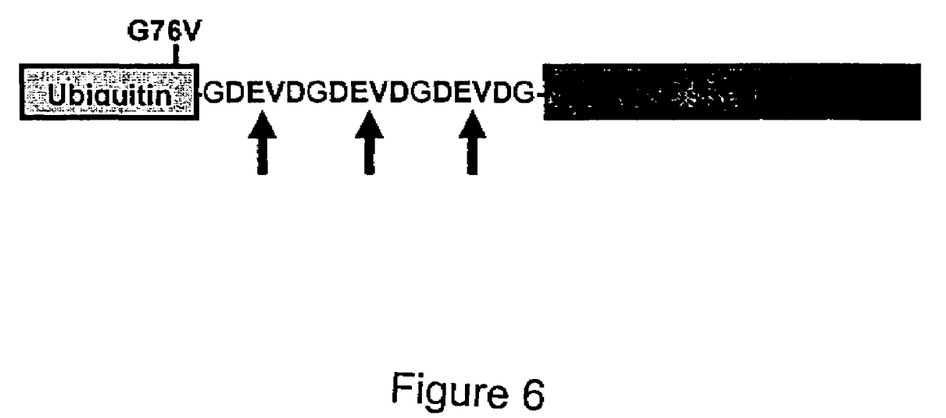
FIG. 6: Schematic illustration of UbG-DEVDsRx, a reporter system that labels apoptotic cells in vivo in zebrafish. The N-terminal part of the marker is a zebrafish ubiquitin moiety with a glycine to valine mutation at position 76 (UbG76V). When fused to the rest of the chimera, UbG76V functions as a nonremovable fusion-degradation signal leading to proteasomal degradation of the entire protein within minutes (see, e.g. Johnson et al. *J. Biol. Chem.* 270, 17442-17456 (1995)). UbG76V is fused to a linker (SEQ ID NO: 2) containing DEVD (SEQ ID NO: 1) recognition motifs (arrows) which are specifically cleaved by effector caspase-3. Finally the C-terminal module is a fluorescent protein. The red fluorescent protein DsRed was preferred to the more widely used green fluorescent protein (GFP) because the tetrameric structure of DsRed confers a remarkable resistance to denaturation (Lindsten et al. *Nat. Biotechnol.* 21, 897-902 (2003)). Consequently, DsRed fluorescence is several fold more stable than that of GFP, even under conditions affecting protein stability (Lindsten et al. *Nat. Biotechnol.* 21, 897-902 (2003)). This is a significant advantage because the apoptotic machinery compromises protein stability. However, wild-type DsRed has a slow maturation rate, which is an inconvenient because apoptosis is a rapid process. To circumvent this problem, we used the DsRed.T1 mutant, which matures 15 times faster than the wild-type protein (maturation half-time: 0.7 h, see, e.g. Kerr et al. *Br. J. Cancer.* 26, 239-257 (1972)). Expression of the complete reporter gene is placed under transcriptional control of the human cytomegalovirus promoter which drives high levels of ubiquitous transgene expression in zebrafish.

In the instant disclosure, we demonstrate the power of the methods and materials of the invention using a transgenic zebrafish model where cells entering the cell death program are labelled in vivo with a fluorescent protein. Specifically, in order to study PCD in developing zebrafish, we used the methods and materials of the invention to create a fluorescent reporter system (UbG-DEVDsRx) where a fusion-degradation signal (ubiquitin mutant UbG76V) (see, e.g. Johnson et al. *J. Biol. Chem.* 270, 17442-17456 (1995)) is fused to DsRed.T1, a fast maturing DsRed variant (Bevis et al. *Nat. Biotechnol.* 20, 83-87 (2002)), by a linker containing DEVD (SEQ ID NO: 1) recognition motifs (FIG. 6). These motifs are specifically cleaved by caspase-3, a primary effector of vertebrate apoptosis (see, e.g. Lazebnik et al. *Nature* 371, 346-347 (1994); and Yabu et al. *Biochem. J.* 360, 39-47 (2001)). In viable cells, the fusion degradation signal ensures that the marker is degraded before the chromophore can adopt its fluorescent conformation (see, e.g. Dantuma et al. *Nat. Biotechnol.* 18, 538-543 (2000); and Lindsten et al. *Nat. Biotechnol.* 21, 897-902 (2003)). In apoptotic cells however, caspase-3 cleaves the linker and removes the degradation signal. DsRed.T1 then escapes proteasomal degradation, matures and labels the cell. Using this model, we show that in mutants and morphants where brain macrophages- or phosphatidylserine receptor-mediated apoptotic-cell recognition is deficient, PCD is impaired. Indeed, developing neurons initiate apoptosis and activate effector caspase-3, but they fail to complete later phases of the cell death program.

BRIEF DESCRIPTION OF THE FIGURES

FIG. 1: Caspase-3-dependent expression of DsRed. (a)-(e) Fluorescence and visible light microscopy images showing live transgenic zebrafish embryos injected with a construct containing a caspase-3 specific cleavage site (a) or a control construct lacking a cleavage site (b)-(c). (d)-(e) Embryo injected with a caspase-3-specific construct and incubated in the caspase-3 inhibitor Z-DEVD-FMK. (f)-(h) In vivo confocal microscopy time series (taken 2 hours apart) showing morphological changes undergone by two skin cells over a 4 hour period. The increase in fluorescence intensity over time is not visible because fluorescence levels in all 3 confocal images have been brought to equal levels to facilitate the observation of cell morphology. (i)-(l) View of a cluster of apoptotic cells. Caspase-3-induced red fluorescence intensity (i) was translated to pseudocolors using the NIH Image software (j). Three cell populations (I, II, III) can be distinguished according to red fluorescence intensity. (k) TUNEL-labeling of the same cells. (l) overlay of pictures (i) and (k).

FIG. 2: Apoptotic neurons in 3 dpf wild-type and panther mutant brains. (a)-(b) Lateral optical sections of UbG-DEVDsRx-generated fluorescence in the wildtype (a) and panther (b) brain. Apoptotic skin cells reveal the outline of the head. Rostral to the right, dorsal to the top. (c)-(h) Higher magnification of redfluorescent labelling (c)-(d) and conversion to pseudocolors (e)-(f) reveal that in panther, a number of highly-fluorescent neurons (arrows) remain TUNELnegative (g)-(h). (i)-(j) are overlays of images (c) and (g), and (d) and (h), respectively. (k) percentage of TUNEL-positive red-fluorescent neurons in wild-type (WT) and panther (Pan) embryos from 1-6 dpf Data represent mean±s.e.m. Asterisk indicates a statistical difference from respective control (P<0.05). Scale bars, (a)-(b) 100 µm; (c) 10 µm.

FIG. 3: Apoptotic neurons in the brain of the PSR morphant. Lateral optical sections of UbG-DEVDsRx-generated fluorescence in embryos injected with a control morpholino-modified oligonucleotide (a) and in the PSR morphant (b) brain. Rostral to the right, dorsal to the top. (c)-(f) Higher magnification of redfluorescent labelling (c) and conversion to pseudocolors (d) reveal that, in the PSR morphant, as in the panther mutant, a number of highly-fluorescent neurons (arrows in (d)-(f)) remain TUNEL-negative (e). (f) is an overlay of images (c) and (e). (g) percentage of TUNEL-positive red-fluorescent neurons from 1-6 dpf in embryos injected with a control morpholino-modified oligonucleotide (Con) and in PSR morphants (PSR). Data represent mean±s.e.m. Asterisk indicates a statistical difference from respective control (P<0.05). Scale bars, (a)-(b) 100 µm; (c) 10 µm.

FIG. 4: Neurons which escape apoptosis in the panther mutant and PSR morphant keep intact protein synthesis capabilities. Lateral optical sections of UbG-DEVDsRx/HuC-d2EGFP-generated fluorescence in the brain of a live embryo injected with a control morpholino-modified oligonucleotide (a). Rostral to the right, dorsal to the top. Both d2EGFP and DsRed.T1 fluorescence patterns are presented. (b) Higher magnification of double-transgenic cells clearly shows that in control embryos, d2EGFP labelling of viable neurons is distinct from DsRed.T1 labelling of apoptotic cells. (c)-(g) d2EGFP-labelling in PSR-morphant (c) and fluorescence analysis (d) reveal that in some DsRed.T1-labelled apoptotic cells ((e) and arrows in (c)-(g)) with high levels of red fluorescence (f) protein synthesis and d2EGFP gene expression are functional. Consequently, these cells appear yellow when images (c) and (e) are merged (g). (h) d2EGFP-positive red-fluorescent neurons are only observed in panther mutants (Pan) and PSR morphants (PSR), not in embryos injected with a control morpholino-modified oligonucleotide (Con). Data represent mean±s.e.m. Asterisk indicates a statistical difference from respective control (P<0.05). Scale bars, (a) 100 µm; (b)-(c) 10 µm.

FIG. 7: Abnormal development and apoptosis patterns in the PSR morphant. (a)-(c), At 30 hpf, the PSR morphant is smaller in size than wildtype embryos of the same age and development is delayed (compare (a) with FIG. 1(b), note the scale difference). Intense UbG-DEVDsRx-generated apoptosis-labelling is observed throughout the embryo (compare (b) with FIG. 1(a)). At higher magnification (c), apoptotic cell aggregates can be observed under visible light because they form dark patches in the brain and trunk (arrows). Development of the forebrain and eye are also abnormal (arrowhead). (d)-(e) 48-hpf PSR morphant (d) and wild-type embryo (e). Abnormal heart structures are observed in the PSR morphant ((d) arrowhead) and, like PSR deficient mice (see, e.g. Li et al. *Science.* 302, 1560-1563 (2003)), this zebrafish morphant exhibits severe brain malformations (arrow). Somites develop in the PSR morphant but the trunk exhibits a bent shape. (f)-(g) 72-hpf PSR morphant (f) and wild-type embryo (g). The size of the PSR morphant is still reduced compared to that of a wild-type of the same age (note scale difference between (f) and (g)), heart and brain structures are still abnormal. (h)-(i) Higher magnification observation of the 72-hpf eye shows that, like in PSR-deficient mice, the eye and lens are smaller in zebrafish PSR morphants (h) than in wild-types (i) and the position of the lens is abnormal (arrow). (j)-(k) Dorsal view of the 80 hpf midbrain (rostral to the left) with staining of PSR-morphant (j) and wild-type (k) macrophages by neutral red (see, e.g. Herbomel et al. *Dev. Biol.* 238, 274-288 (2001)). Unlike panther macrophages, PSR-morphant macrophages colonize the brain. PSR morphants die between 6 and 8 dpf. Scale bars, (a) 150 μm; (c) 75 μm, (d)-(g); 250 μm; (h)-(k) 50 μm.

DETAILED DESCRIPTION OF THE INVENTION

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

"Treatment" or "therapy" refer to both therapeutic treatment and prophylactic or preventative measures.

The term "therapeutically effective amount" refers to an amount of a drug or other agent effective to treat a disease or disorder in a mammal. In the case of cancer for example, a therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

Cytokines provide an example of a therapeutically active polypeptide. The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines A. Overview As noted above, there is a need in the art to understand the physiology of proteolytic processes. This need has increased markedly in recent years as artisans seek efficient bioassays that can for example determine the role of proteases in both normal cellular processes as well as in the context of specific diseases. The invention disclosed herein satisfies this need by providing a novel way to detect virtually any protease activity in cell cultures and in whole organisms. The invention can therefore be used for example to screen for drugs or genes modulating a specific proteolytic activity.

Another and related purpose of the present invention is to specifically deliver therapeutic peptides or proteins to cells or tissues exhibiting a proteolytic activity of choice. For example, the present invention could be used for the delivery of antimicrobial peptides or specific inhibitors only to cells infected by a particular pathogen.

Bioassays to directly monitor protease activities in vivo use fluorescent protease substrates which can be divided into two categories: fluorophore-coupled peptide- and reporter protein-based assays. Fluorophore-coupled peptide-based assays use a donor and an acceptor fluorophore linked to each other by a synthetic peptide containing a protease cleavage site (see, e.g. Bark et al., (2000) Methods 20:429-435). In the absence of protease activity, the two fluorophores are maintained close to each other by the linker peptide and fluorescence resonance energy transfer (FRET) occurs from the donor to the acceptor. When the linker peptide is cleaved by the protease of interest, the donor and acceptor fluorophores are separated, FRET does not occur anymore and fluorescence emission from the donor increases at the expense of fluorescence emission from the acceptor. Measurement of fluorescence variations is used to assay protease activity.

Fluorophore-coupled peptides present a number of limitations. These peptides do not diffuse across membranes and therefore they can only be used in purified samples in vitro or in cell cultures after microinjection. Most proteases use full-length proteins, not peptides, as substrates. However, full-length proteins are difficult to label with two different fluorophores. Therefore, the relevance of these peptide-based assays to physiological conditions is limited. Fluorophore-coupled peptide-based assays do not require information on the crystal structure of the protease, which is a major improvement over previous methods, but the sequence of the cleavage site within a target protein needs to be determined to design the linker peptide sequence.

Reporter protein-based assays use chimeric genes coding for two fluorescent proteins linked to each other by a protease substrate, which can be all or part of a protein. As with fluorophore-coupled peptides, the measurement of FRET between the two fluorescent proteins is used to assay protease activity. This method presents major improvements over the use of fluorophore-coupled peptides because small full-length proteins can often be used as substrates and chimeric genes can be expressed in cells or transgenic organisms. Therefore, protease activities can be measured directly in vivo (see, e.g. Felber et al., (2004) Biotechniques 36:878-885).

However, the measurement of FRET to assay protease activity limits the use of this method because (i) certain FRET donors such as the blue fluorescent protein (BFP) are excited by UV light which causes cellular damage or (ii) the excitation spectrum of the donor overlaps with the emission spectrum of the acceptor. Therefore, subtle changes in energy transfer are difficult to quantify. This strongly limits the sensitivity of the assay (see, e.g. Mitra et al., (1996) Gene. 173: 13-17; Pollok et al., (1999) Trends Cell Biol. 9:57-60; and Truong et al., (2001) Curr Opin Struct Biol. 11:573-578).

Delivery of Therapeutic Agents

An important drawback of currently available drugs is that common routes of application (oral, nasal, subcutaneous or intravenous) are systemic. Therefore, single or repeated drug delivery encounters the problems of nonspecific distribution, systemic side effects, premature degradation and limited drug resorbtion. In this context, a major challenge of modern medical therapy is the design of drugs, which become activated exclusively at the target site, interfere specifically with key mechanisms of a particular disease and present little or no side-effects. The need for such drugs has become particularly evident for chronic diseases such as cancer and immune-mediated inflammatory diseases, which usually require long-term treatments and can be complicated by relapses and severe drug side effects (see, e.g. Tarner et al., (2003) Ann N Y Acad Sci. 998:512-519).

Novel strategies aiming at designing targeted therapeutics can be divided into two categories: a first category seeks to optimize application techniques for drugs that use common routes of delivery. These use the conjugation of therapeutic agents to antibodies or absorption enhancers, the use of encapsulation techniques or nanotechnology. A second major category uses gene therapy, which allows long-term production of therapeutic molecules in vivo in specific tissues. Gene therapy uses vectors (e.g. engineered viruses) to deliver DNA constructs where specific gene promoters target the expression of therapeutic agents to specific cell types (see, e.g. Thomas et al., (2003) Nat Rev Genet. 4:346-358; and Yoshida et al., (2004) Cancer Sci. 95:283-289).

The present invention provides a way to further enhance the specificity of these strategies by targeting the delivery of therapeutic agents only to diseased cells within a specific cell type. Healthy cells within the same cell type are left drug-free.

Functional Attributes of Invention

In eukaryotic cells, the level of normal regulatory proteins and the removal of mutant, misfolded and damaged proteins are tightly controlled by an evolutionary conserved degradation complex called the proteasome. Certain proteins contain endogenous degradation signals, which make them susceptible to proteasomal degradation. Other proteins are recognized by the ubiquitin-conjugating system which labels them with ubiquitin, a 76 amino-acid tag acting as a degradation signal to promote the rapid breakdown of proteins by the proteasome. The half-life of a ubiquitin-coupled protein is usually reduced to a few minutes.

By fusing a protein to a ubiquitin moiety or any other degradation signal, it is now possible to engineer virtually any protein to transform it into a proteasome substrate. Depending on the degradation signal used, the half-life of these chimeric proteins can be reduced to a few minutes. As an example, recent work in cell cultures and transgenic mice showed that the half life of ubiquitin-GFP chimeras is so short that GFP does not have time to adopt its fluorescent conformation and cells remain unlabelled unless proteasomal activity is artificially inhibited (see, e.g. Dantuma et al., (2000). Nat Biotechnol. 18:538-543; and Lindsten et al., (2003) Nat Biotechnol. 21:897-902).

Figure 5:
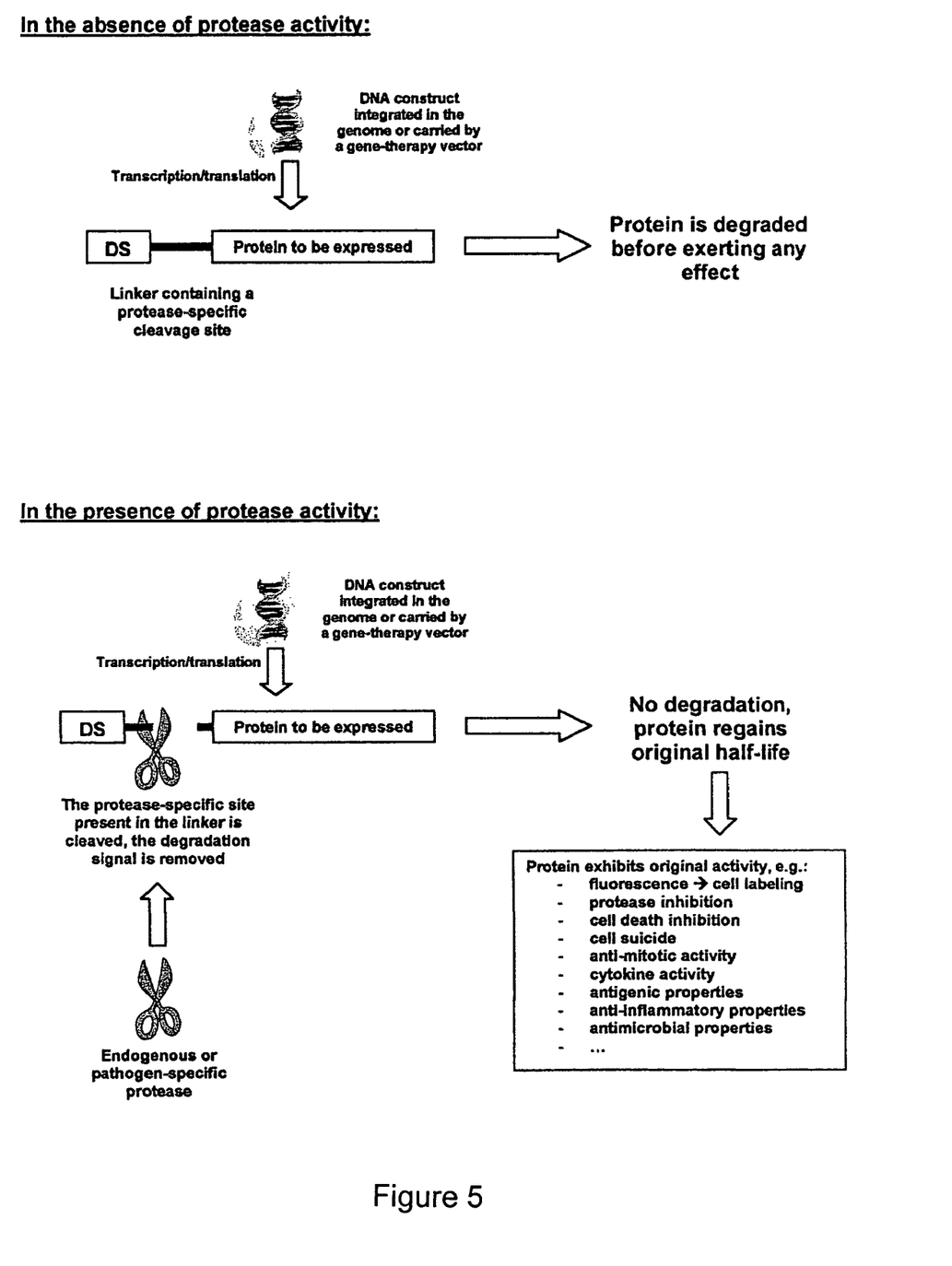
FIG. 5: Schematic illustration of protease-mediated protein expression system. "DS"=degradation signal.

The present invention takes advantage of the short half-life of degradation signal-coupled proteins to restrict the expression of reporter or therapeutic proteins to cells exhibiting a specific protease activity. The invention is a construct where a protein (e.g. reporter protein or therapeutic agent) is fused to a degradation signal by a linker which contains a specific protease cleavage site. In cells where the proteolytic activity of choice is absent, the degradation signal stays fused to the rest of the protein and the whole chimera is degraded within a few minutes following translation. In cells where a specific protease is activated, the linker is cleaved and the degradation signal is removed from the rest of the fusion protein. The reporter protein or therapeutic agent can then live long enough to label the cell or exert therapeutic properties (FIG. 5).

As noted above, embodiments of the present system can be expressed using DNA expression vectors. Therefore, it can be carried by gene therapy vectors. It can also be used to assay protease activity in vivo which is a major improvement over in vitro approaches such as crystal-structure-based studies. In addition, diffusion across cell membranes is not a problem which is an improvement over the use of fluorophore-coupled peptides.

The present system does not require use of FRET. This is advantageous over other proteolysis bioassays because differences between cells exhibiting a specific protease activity (fluorescent or labeled cells) and other cells (unlabeled cells)

are greater. Therefore, contrary to FRET-based techniques, the sensitivity of the bioassay is not limited by overlapping fluorescence spectra between donors and acceptor fluorescent molecules. In addition, unlike FRET-based systems, the degradation signal and the protein to be expressed can be far from each other. Full-length proteins of virtually any size can be used as linkers, therefore protease substrates can be very similar to their natural counterparts. Because full-length substrates can be used, there is no need to know the exact sequence recognized by a specific protease. Knowing that a particular protein is specifically cleaved by a protease of interest is enough to generate the construct since that particular protein can be used as a linker.

Because virtually any amino-acid sequence can be used as a linker and the degradation signal can be placed at the N- or C-terminus of the protein to be expressed, signal peptides and transmembrane domains can be added to the present system. This is an improvement over other techniques because it enables bioassays that target proteases located in membranes or vesicles.

Finally, if the present system is carried by a vector to express a therapeutic agent, drug delivery is spatially and temporally controlled by the protease of interest. By introducing a disease- or pathogen-specific protease cleavage site in the linker, drug delivery can be limited to diseased cells only. This is a major improvement over common routes of drug application (oral, nasal, subcutaneous or intravenous). It also provides a critical increase in the specificity of gene therapy systems, which usually can only target drug delivery to a specific cell type, not to diseased cells within a given cell type.

As discussed in detail below, the invention was tested by making a construct where the degradation signal is a non-removable ubiquitin moiety (G76V zebrafish ubiquitin mutant) fused to the red fluorescent protein DsRed Express by a linker containing a caspase-3 cleavage site (amino acid sequence: DEVD; SEQ ID NO: 1). Caspase-3 is activated when a cell starts executing a programmed cell-death (apoptosis) process. The expression of the chimeric gene was put under the control of they cytomegalovirus immediate early promoter, which has the ability to drive strong gene expression in a very wide range of cell-types in zebrafish. The DNA construct was microinjected in one-cell-stage zebrafish embryos to generate transgenic fish where apoptotic cells express the red fluorescent marker.

Figure 1:
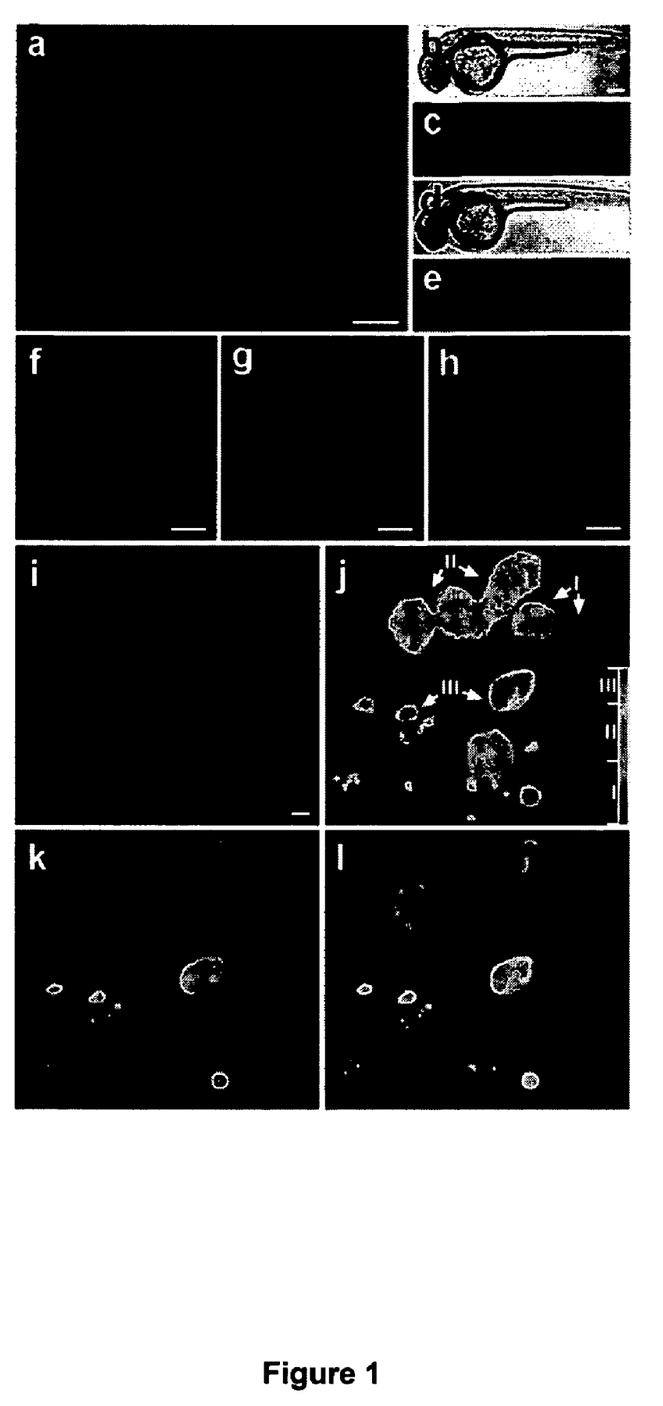

A summary of results are shown in FIG. 1. FIG. 1a shows that the present invention can be used in vivo in zebrafish. The test construct labels a wide range of cell types throughout the embryo. A control embryo (FIG. 1b) injected with a construct where the linker does not contain a cleavage site doesn't express any detectable red fluorescence (FIG. 1c). This indicates that when the degradation signal cannot be removed, the chimeric protein is rapidly degraded, DsRed does not have time to acquire its fluorescent conformation and the system doesn't generate any background fluorescence. Embryo injected with the test construct (FIG. 1d) and incubated in the presence of the caspase-3 inhibitor Z-DEVD-FMK (75 μM) does not express any fluorescence either (FIG. 1e), indicating that the expression of red fluorescence is specifically controlled by caspase-3.

FIGS. 1f-h show two red fluorescent skin cells. Pictures were taken 2 hours apart in a live embryo. Progressive morphological alterations typical of apoptosis can be observed: in FIG. 1f, the two skin cells still exhibit their typical, almost geometric structure and the intercellular junction is still regular. Two hours later (FIG. 1g), the cells have shrunk dramatically and after 4 hours (FIG. 1h), their morphology has completely changed. One of the cells has broken up into cell bodies. In FIGS. 1f-h, fluorescence intensity has been optimized so that morphological alterations in cell morphology can be observed. In contrast, FIG. 1i shows a cluster of apoptotic skin cells and relative differences in red fluorescence intensity can be observed. In FIG. 1j, red fluorescence intensity was converted into pseudocolors using the NIH Image software. This reveals that three populations of cells (marked I, II and III) can clearly be distinguished according to red fluorescence intensity. DsRed fluorescence is known to increase as the protein matures and its concentration increases. Therefore, red-fluorescence intensity is likely to be lower during early phases of the apoptotic process, when caspase-3 activation starts, and higher during late phases of apoptosis. To determine whether red fluorescence could serve as a molecular timer of the apoptotic program, cells were co-labeled by terminal deoxynucleotidyl transferase (TdT)-mediated dUTP nick-end labeling (TUNEL, FIG. 1k-l), a widely used marker of DNA strand breaks generated specifically during late apoptosis. Comparison of FIGS. 1i-j and 1k-l shows that cell population I, which exhibits low red fluorescence intensity, is TUNEL-negative. This indicates that in these cells, caspase-3 has been activated but the apoptotic program has not yet reached a phase where DNA strands are altered. Population II, which exhibits a medium level of red fluorescence, is slightly labeled by TUNEL indicating that in this population, alteration of DNA structure has started. Population III, which exhibits high levels of red fluorescence, is strongly labeled by TUNEL. In addition, these cells tend to form cell bodies and present the pyknotic morphology characteristic of late apoptotic cells. Therefore, the intensity of red fluorescence increases during the apoptotic program and the present construct can be used to distinguish cells entering an apoptotic state from cells where the cell death program has reached a later phase.

Taken together, these results indicate that, using the present invention, protease-controlled protein expression can be achieved in a wide range of cell types in a whole organism. Furthermore, the present invention is relevant to another aspect of medical therapy: the improvement of drug delivery methods. As DNA vectors for gene therapy evolve and become more reliable, the need for the specific delivery of active agents expressed by these vectors will increase. The present invention has the potential to meet such a need and facilitate the design of cell- or disease-specific drugs.

B. ILLUSTRATIVE EMBODIMENTS OF THE INVENTION

The present invention provides methods and materials that can be used to assess and exploit protease mediated protein expression. An illustrative embodiment of the invention is a polynucleotide (preferably one that is present on a vector such as a plasmid) encoding a polypeptide having a plurality of operatively linked elements comprising a polypeptide degradation signal that functions as a proteosome substrate; a polypeptide having an observable activity; and a linker disposed between the polypeptide degradation signal and the polypeptide having an observable activity.

In this embodiment, the linker comprises a protease recognition motif that is capable of being specifically recognized and cleaved by a protease; so that in the presence of the protease the polypeptide degradation signal is cleaved from the polypeptide having an observable activity so that the polypeptide having an observable activity is not susceptible to proteasomal degradation; and in the absence of the protease the polypeptide degradation signal is operatively linked to the polypeptide having an observable activity so that the polypeptide having an observable activity is susceptible to proteasomal degradation; so that the activity of the polypeptide having an observable activity is observed when the polypeptide motif is specifically recognized and cleaved by the protease; and the activity of the polypeptide having an observable activity is decreased or not observed when the polypeptide motif is not specifically recognized and cleaved by the protease.

Artisans are familiar with a variety of elements that can be used to construct embodiments of the claimed invention.

DNA Constructs

Embodiments of the present system include DNA constructs such as plasmids. The DNA constructs can be carried by expression or gene-therapy vectors or used to make transgenic organisms and cell lines. Virtually any cell-specific or ubiquitous promoter can drive the expression of the DNA constructs. The construct can be expressed in protein-expression systems to generate purified chimeric proteins which can be used as drugs or in research-oriented applications.

Degradation Signal

The degradation signal can be a wild-type or mutant ubiquitin moiety or any other degradation signal that can alter the half-life of the protein to be expressed. Different degradation signals lead to different degradation kinetics of the three-module system (signal/linker/polypeptide). Therefore, different degradation signals can be selected to customize the invention for specific applications where protein degradation kinetics are important. CL-1 degron refers to widely used destabilizing signals for fluorescent proteins and other reporters. See Bence NF, Sampat RM, Kopito RR, Science, 2001, 292(5521):1552-5. F-boxes and SCF substrates are also possible degradation signals that can be used in this system. Nakayama KI, Nakayama K, Semin. Cell Dev. Biol., 2005, June; 16(3):323-33. Degradation domains such as that of the mouse ornithine decarboxylase degradation domain are also becoming more widely used. See Li X, et al., J. Biol. Chem., 1998, 273(52):34970-5.

In addition, those skilled in the art are familiar with various protein degradation signals that can function as a proteasome substrate. For example, a description of murine and human ubiquitins can be found in Passmore LA, Barford D., Biochem. J., 2004, May 1; 379(Pt 3):513-25. A description of murine and human ubiquitins can be found in Gilon T, Chomsky O, Kulka RG, EMBO J., 1998 May 15; 17(10):2759-66.

A description of PEST sequences can be found in Rechsteiner M, Rogers SW, Trends Biochem Sci. 1996 July; 21(7): 267-71. A description of KFERQ signals can be found in Dice J F., Trends Biochem. Sci. 1990 August; 15(8):305-9.

A description of Cyclin destruction boxes can be found in Glotzer M, Murray AW, Kirschner MW. Cyclin is degraded by the ubiquitin pathway. Nature. 1991 Jan. 10; 349(6305): 132-8.

Linker

The linker can be all or part of a protein known to contain a cleavage site recognized by the protease of interest. As is known in the art, a very large number of protease-specific motifs have been described. The present technique permits use of a whole protein as a protease substrate, without the need to know the exact protease recognition motif sequence.

A description of protease recognition motifs that are capable of being specifically recognized and cleaved by a protease such as murine and human DEVD (Asp-Glu-Val-Asp; SEQ ID NO: 1) motifs can be found in the Fischer et al reference cited immediately below. This paper describes 280 motifs (including DEVD; SEQ ID NO: 1) which are recognized by caspases. (Fischer U, Janicke RU, Schulze-Osthoff K, Cell Death Differ. 2003 January; 10(1):76-100. A description of Presenilins, BACE and Alzheimer disease-related proteases can be found in Hooper NM, Turner AJ, Biochem Soc Trans. 2000; 28(4):441-6. A description of Proprotein and prohormone convertases can be found in Seidah NG, Chretien M, Brain Res. 1999 Nov. 27; 848(1-2):45-62. A description of proteases responsible for pathogen activation can be found in Kido, H et al., Mol. Cells, 1999 Jun. 30; 9(3):235-44. See also, Tonello F, Morante S, Rossetto O, Schiavo G, Montecucco C, Adv. Exp. Med. Biol., 1996; 389:251-60; and Pettit SC, Everitt LE, Choudhury S, Dunn BM, Kaplan AH, J. Virol., 2004 August; 78(16):8477-85.

Protein or Polypeptide of Interest

The protein to be expressed upon proteolytic removal of the degradation signal can be a reporter protein, a therapeutic agent or virtually any protein of interest. If the protein to be expressed is a reporter protein, cell lines or transgenic organisms can be used to screen in vivo for drugs or genes modulating the activity of the protease of interest. The selection of the polypeptide of interest can be tailored to suit a broad range of detection methods and applications.

Typical reporter proteins include those known in the art such as Beta galactosidase, Luciferase as well as fluorescent proteins. Fluorescent proteins of interest include, but are not limited to, GFP, CFP, RFP, YFP, Kaede, Emerald, Venus, DsRed, mHoneydew, mBanana, mOrange, tdTomato, mTangerine, mStrawberry and mCherry (Shaner NC et al., Nat. Biotechnol., 2004, 22(12):1567-72).

Typical therapeutically active polypeptides include molecules such as protease inhibitors, cell death inhibitors, peptides with anti-mitotic activity, cytokines, peptides with antigenic properties, anti-inflammatory peptides, antimicrobial peptides and the like. The present invention can also be used for the specific delivery or expression of antigens and antibodies and confer resistance against various pathogens (Tegerstedt K et al., Anticancer Res., 2005, 25(4):2601-8).

Recent studies on the molecular mechanism of dopaminergic cell loss in Parkinson's disease point to antioxidative mechanisms and the use of growth factors and transporters to reduce neurodegeneration in animal models and patients. These studies suggest that future therapeutic strategies may require specific expression of a number of Parkinson's disease-related proteins (see Sun M et al., Hum. Gene Ther., 2004, 15(12):1177-96; Yamada M et al., Hum. Gene Ther., 2005, 16(2):262-70; Lo Bianco C et al., PNAS, 2004, 101 (50):17510-5, for example). The present invention can be used in gene therapy applications to enhance antioxidative functions and express growth factors or transporters in diseased cells. In these cases, proteins of interest would be:

(a) catalase, superoxide dismutase and glutathione S-transferase, which metabolize oxidative radicals (Tabner BJ et al., Free Radic. Biol. Med., 2002, 32(11):1076-83; Whitworth AJ et al., PNAS, 2005, 31; 102(22):8024-9);

(b) vesicular monoamine transporters (Sun M et al., Hum. Gene Ther., 2004, 15(12):1177-96) or the dopamine transporter (Bannon MJ, Toxicol. Appl. Pharmacol., 2005, 204(3):355-60), which are involved in dopamine synaptic release and storage;

(c) UCH-L1 and its S18Y mutant, which is protective against certain forms of Parkinson's disease (Liu Y et al., Cell. 2002, 111(2):209-18);

(d) Parkin, which, when overexpressed, confers resistance to dopaminergic neurodegeneration (Yamada M et al., Hum. Gene Ther., 2005, 16(2):262-70; Lo Bianco C et al., PNAS, 2004, 101(50):17510-5);

(e) GTP cyclohydrolase 1 which contributes to L-dopa synthesis and reverses dyskinesia symptoms when overexpressed (Carlsson T et al, Brain. 2005, 128(Pt 3):559-69);

(f) stress proteins, which improve protein maturation and exert anti-apoptotic effects in models of Parkinson's disease (Dong Z et al., Mol. Ther., 2005, 11 (1):80-8);

(g) growth factors and their receptors, which exert antiparkinsonism effects and reduce dopaminergic cell loss (Wang X et al., Brain Res. Mol. Brain Res., 2005, 139 (1):88-102).

Methods

The invention provides various methods that exploit the protease-regulated polypeptide described herein. The methods can be used to detect protease activity and/or to take advantage of protease-mediated expression to achieve controlled delivery of a polypeptide to target cells. One such method is a method of testing an environment for the presence of a protease. The method comprises placing the protease-regulated polypeptide in the environment and observing the presence or absence of the observable activity of the polypeptide of interest, wherein the presence of the observable activity is indicative of the presence of the protease. Another embodiment of the invention is a method of examining the ability of a compound to modulate the activity of a protease comprising exposing the protease-regulated polypeptide to the protease and observing the presence or absence of the observable activity of the polypeptide of interest; and then comparing the activity so observed to the activity of the polypeptide of interest that is observed when the protease-regulated polypeptide is exposed to the protease in combination with the compound to be examined so that the compound's ability to modulate the activity of the protease is examined.

Yet another embodiment of the invention is a method of delivering a polypeptide of interest to a cell having a known protease activity. The known protease activity may be endogenous or one that has been introduced into the cell. The method comprises placing the protease-regulated polypeptide within a cell having the known protease activity. The linker in the polypeptide comprises a protease recognition motif that is specifically recognized and cleaved by the known protease activity so that the polypeptide of interest is delivered to the cell. Optionally, the polypeptide of interest is a reporter protein and/or a therapeutically active polypeptide. Such methods can be useful both for therapeutic manipulation of a cell and for screening and developing therapeutic methods, for example, in an in vitro or animal model of a particular disease state or condition to be studied.

Kits

The invention also provides articles of manufacture and kits which include the materials of the invention disclosed herein. Typically, a nucleotide or polypeptide of the invention is provided with, or inside of, a container. Optionally, such articles of manufacture and kits further include instructions for using the disclosed materials of the invention.

C. SPECIFIC EMBODIMENT OF THE INVENTION

Using the disclosed invention to study PCD in developing zebrafish, we created a fluorescent reporter system (UbG-DEVDsRx) where a fusion-degradation signal (ubiquitin mutant UbG76V) (see, e.g. Johnson et al. *J. Biol. Chem.* 270, 17442-17456 (1995)) is fused to DsRed.T1, a fast maturing DsRed variant (Bevis et al. *Nat. Biotechnol.* 20, 83-87 (2002)), by a linker containing DEVD (SEQ ID NO: 1) recognition motifs (FIG. 1). These motifs are specifically cleaved by caspase-3, a primary effector of vertebrate apoptosis (see, e.g. Lazebnik et al. *Nature* 371, 346-347 (1994); and Yabu et al. *Biochem. J.* 360, 39-47 (2001)). In viable cells, the fusion degradation signal ensures that the marker is degraded before the chromophore can adopt its fluorescent conformation (see, e.g. Dantuma et al. *Nat. Biotechnol.* 18, 538-543 (2000); and Lindsten et al. *Nat. Biotechnol.* 21, 897-902 (2003)). In apoptotic cells however, caspase-3 cleaves the linker and removes the degradation signal. DsRed.T1 then escapes proteasomal degradation, matures and labels the cell.

This system labels a wide range of cells throughout living transgenic embryos (FIG. 1a). In contrast, fluorescence is absent when embryos are exposed to the caspase-3 inhibitor Z-DEVD-FMK (FIG. 1b, c), indicating that labelling is specific for cells where caspase-3 is activated. Specific labelling of apoptotic cells by UbG-DEVDsRx depends on a functional proteasomal degradation pathway because failure to degrade the UbG76V-tagged chimera would allow fluorescence to develop, even in the absence of caspase-3 activity. However fluorescence is not detected with control constructs where DEVD (SEQ ID NO: 1) sites are not included in the UbG76V-DsRed.T1 linker (FIG. 1d, e). This is consistent with results obtained in mice expressing a UbG76V-GFP transgene to monitor proteasome activity (see, e.g. Lindsten et al. *Nat. Biotechnol.* 21, 897-902 (2003)). In these mice, in vivo fluorescence only became apparent after prolonged treatment with high concentrations of proteasome inhibitors (see, e.g. Lindsten et al. *Nat. Biotechnol.* 21, 897-902 (2003)). Very high levels of proteasome inhibition are probably necessary to increase the degradation half-time of UbG76V-tagged proteins from minutes to >0.7h, the maturation half-time of DsRed.T18. Since proteasome function is critical for cell survival, cells may die before such levels of inhibition can be reached and thus fluorescence is not detected.

Determining the specificity of our marker for apoptotic cells was facilitated by the observation of morphological changes in skin cells. FIGS. 1f-h show that DsRed.T1-labelled skin cells rapidly lose their typical, almost geometric shape and undergo shrinkage, blebbing and final shedding of cell bodies characteristic of apoptosis (see, e.g. Kerr et al. *Br. J. Cancer.* 26, 239-257 (1972)). Redfluorescent skin cells are also labelled by the TUNEL reaction (FIG. 1i-l) indicating DNA-fragmentation, a late apoptotic event. Taken together, these results confirm that the present marker is specific for apoptotic cells. Since DsRed.T1 fluorescence intensity increases as the chromophore matures (see, e.g. Bevis et al. *Nat. Biotechnol.* 20, 83-87 (2002); and Verkhusha, V. V., et al. *Biochemisty* 42, 7879-7884 (2003)), our system also helps differentiate early apoptotic cells, which exhibit low levels of red fluorescence, from late, TUNELpositive, apoptotic cells where red fluorescence reaches maximal levels (FIG. 1i, l).

Figure 2:
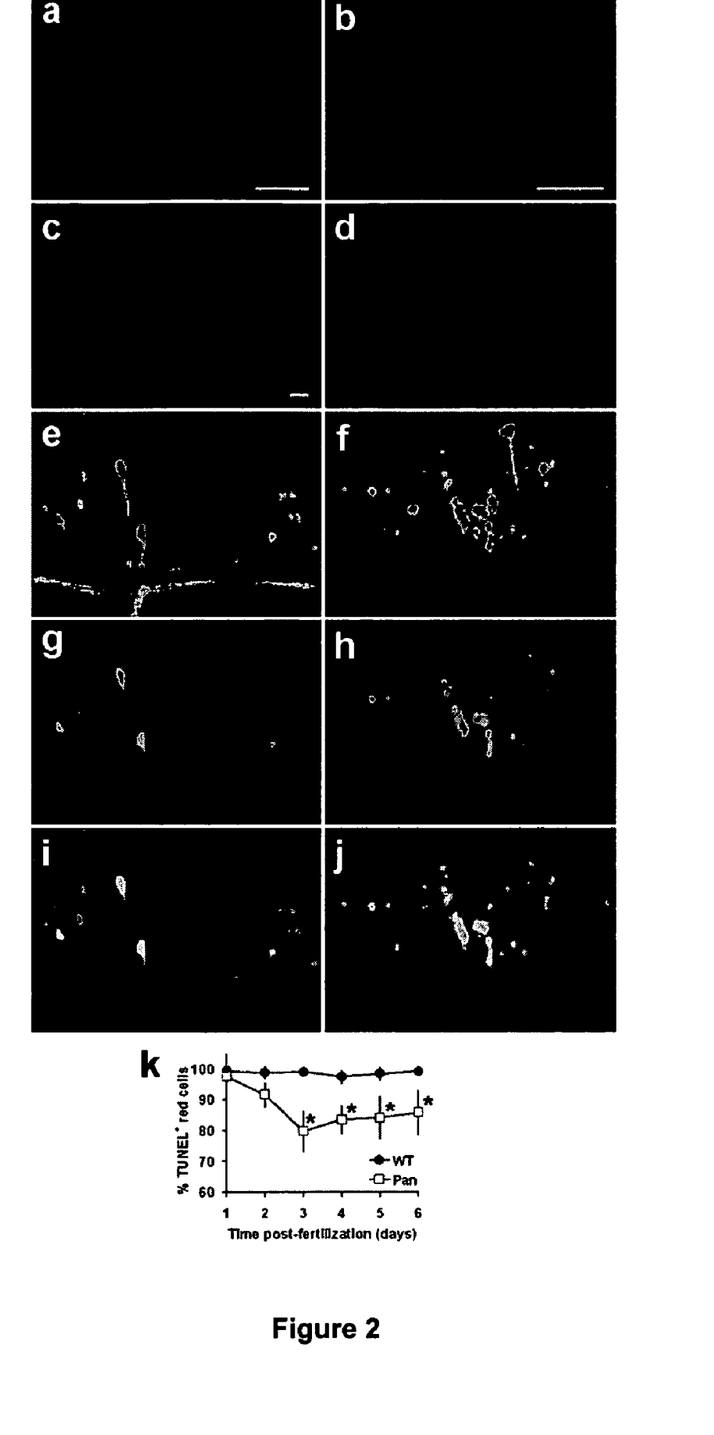

Interestingly, UbG-DEVDsRx labelling is widely distributed in developing neurons 2 to 3 days post-fertilization (dfp; FIG. 2). This is consistent with previous studies showing that neurons die in large numbers during development (see, e.g. Putcha et al. *Cell Death Differ.* 11, 38-48 (2004); Cole et al. *Dev. Biol.* 240, 123-142 (2001); andYuan, J. & Yankner, B. A. *Nature* 407, 802-809 (2000)). In contrast to skin cells however, the majority of red fluorescent neurons (93.42±5.34%) were also TUNEL-positive in 3 dpf embryos (FIG. 2a, c, e, g, l, k), suggesting that in neurons, DNA degradation occurs more rapidly after caspase-3 activation. We became particularly interested in apoptotic cell clearance in the developing brain because the proportion of highly fluorescent cells was significantly lower in neurons (12.59±6.22% of red fluorescent neurons) than in other cell populations such as skin cells (37.93±9.71% of red fluorescent skin cells), which may indicate that apoptotic neurons are cleared faster than other cell populations. To clarify the role of apoptotic cell clearance in the developing brain, we expressed UbG-DEVDsRx in the panther mutant characterized by macrophage colony-stimulating factor (M-CSF) receptor deficiency (see, e.g. Parichy et al. *Development* 127, 3031-3044 (2000)). Previous studies showed that while wild-type zebrafish macrophages start colonizing the brain at 1.5 dpf, panther macrophages totally fail to penetrate brain tissues until about 4 dpf (see, e.g. Herbomel et al. *Dev. Biol.* 238, 274-288 (2001)). This results in the accumulation of apoptotic bodies from 2 dpf until apoptotic cell clearance begins at 4 dpf (see, e.g. Hoeppner et al. *Nature* 412, 202-206 (2001)). Consequently, 3 dpf panther transgenics contain higher numbers of red-fluorescent neurons than wild-types (FIG. 2a, b). The proportion of highly fluorescent neurons is also greater in mutant (58.23±8.47% of red fluorescent neurons) than in wild-type embryos. This confirms that in wild-type zebrafish, mactophage-mediated apoptotic cell clearance occurs quickly and prevents the accumulation of late apoptotic neurons.

Figure 3:
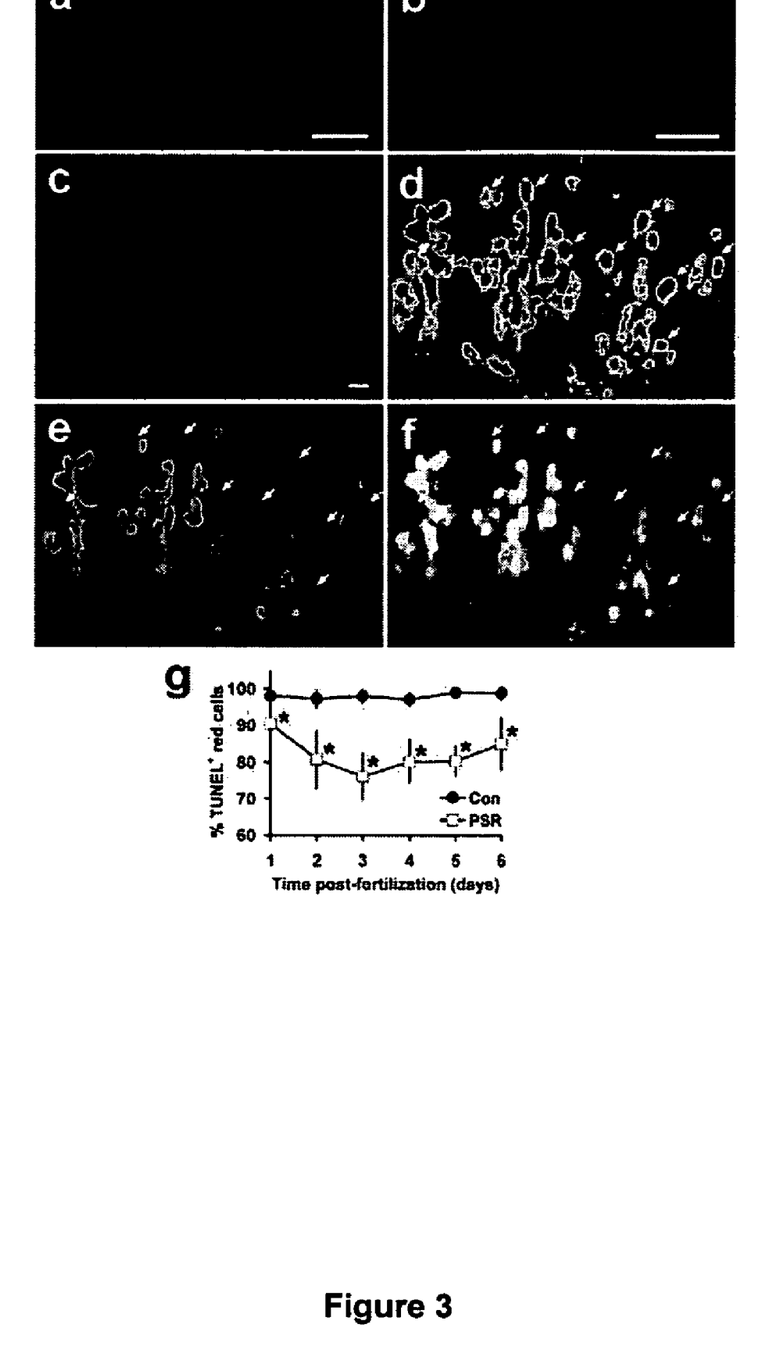
Figure 4:
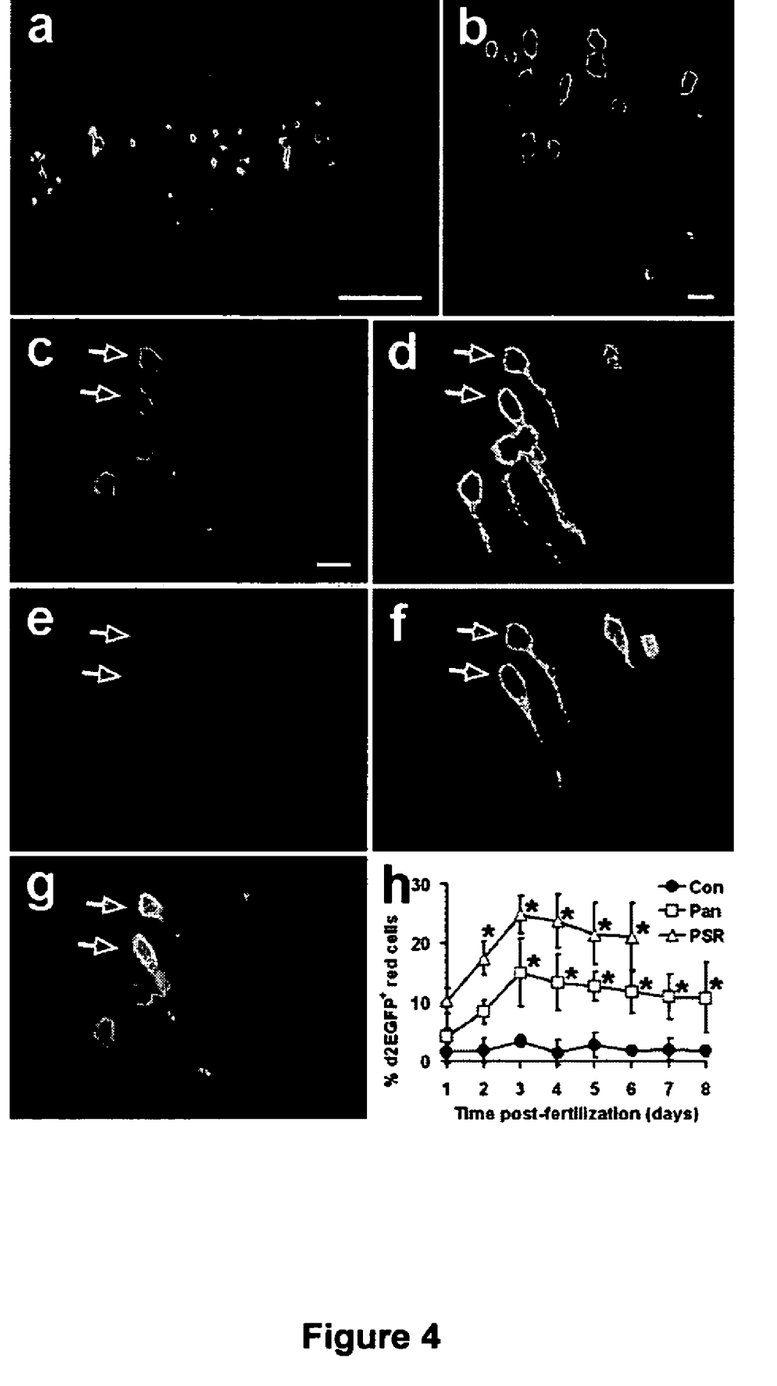
Figure 7:
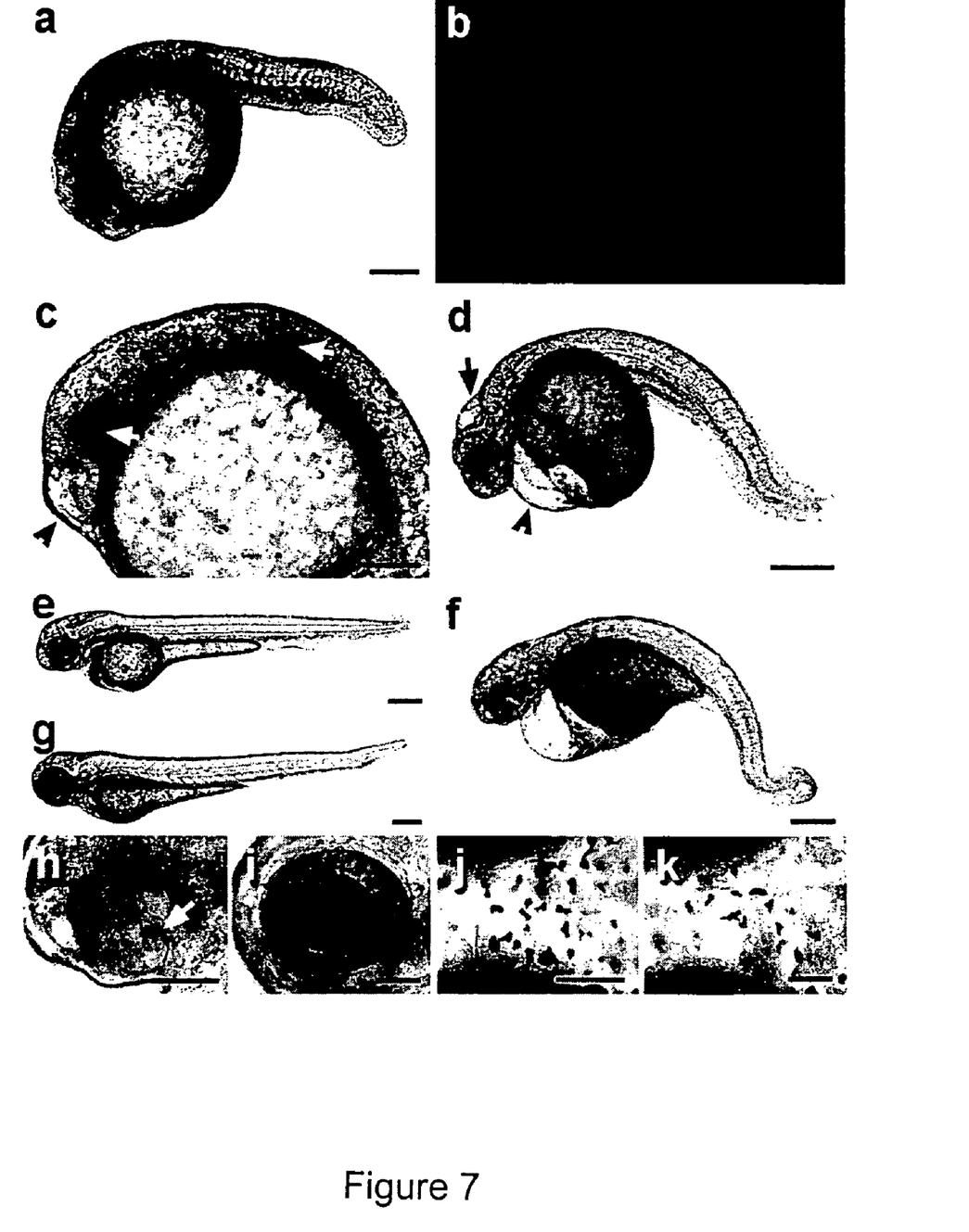

Surprisingly and in contrast to wild-types, 20.19±6.65% of 3 dpf panther neurons exhibiting high levels of red fluorescence remain TUNEL-negative (FIG. 2j, k), suggesting that, in the absence of brain macrophages, some neurons start a cell death program and activate caspase-3 but apoptosis does not proceed to phases where DNA fragmentation occurs. Interestingly, in *C. elegans*, apoptotic cells with weak effector caspase ced-3 activity can recover and survive in engulfment-defective mutants (see, e.g. Hoeppner et al. *Nature* 412, 202-206 (2001); and Reddien et al. *Nature*. 412, 198-202 (2001)). These data are consistent with the idea that caspase-dependent events might be reversible and the completion of PCD requires phagocytes. However, the relevance of these observations to vertebrates and normal physiological conditions remains to be determined because engulfment deficiency only prevents apoptosis in *C. elegans* mutants with limited ced-3 activity, not in wild-type worms. Cells dying by apoptosis express signalling molecules to promote the ultimate phases of PCD: recognition and clearance of cellular remains by phagocytic scavengers such as macrophages (see, e.g. Savill et al. *Nature* 407, 784-788 (2000); and Savill et al. *Nat. Rev. Immunol.* 2, 965-975 (2002). Recent studies have identified the phosphatidylserine receptor (PSR) as essential the recognition and clearance of apoptotic cells both in *C. elegans* and mouse (see, e.g. Wang, X., et al. *Science* 302, 1563-1566 (2003); and Li et al. *Science*. 302, 1560-1563 (2003)). PSR-deficiency causes an accumulation of dead cells in the lung and brain, abnormal development and neonatal lethality in mouse (Li et al., *Science.* 302, 1560-1563 (2003)). Unexpectedly, a fraction of PSR-deficient mice also exhibits a hyperplasic brain phenotype reminiscent of that seen in animals lacking the Apaf-1-caspase-9-caspase-3 apoptosome pathway (see, e.g. Li et al., *Science.* 302, 1560-1563 (2003)). These data and ours converge to show that the absence of apoptotic-cell recognition by macrophages may disrupt PCD in vertebrates. However, results obtained here in the panther mutant, suggest that PCD disruption occurs downstream of the Apaf-1-caspase-9-caspase-3 cascade because the presence of macrophages is not required for the activation of caspase-3 in neurons (FIG. 2). To compare the effects of the panther mutation and PSR deficiency on PCD, we generated PSR-deficient zebrafish embryos using antisense morpholino-modified oligonucleotides (see, e.g. Nasevicius, A. & Ekker, S. C. *Nat. Genet.* 26, 216-220 (2000)). Massive accumulation of apoptotic cells can be observed in PSR morphants and, like PSR-deficient mice, these animals present abnormal brain structures and developmental defects (FIG. 7). FIG. 3 shows that red-fluorescent late-apoptotic cells accumulate in the PSR-morphant brain (FIG. 3). As in panther, a fraction of red-fluorescent cells remain TUNEL-negative (FIG. 3c-g) establishing that during brain development, the presence of macrophages and PSR signalling is dispensable for the activation of caspase-3 but not for the completion of later phases of the apoptotic program. Studies in mice have shown that, other than apoptotic cell recognition, PSR deficiency does not seem to alter phagocyte functions (see, e.g. Li et al. *Science*. 302, 1560-1563 (2003), and macrophage migration is normal in the PSR-morphant brain (FIG. 7j, k). Thus, unlike panther mutants and in vitro preparations where phagocytes are totally depleted (see, e.g. Marin-Teva, J. L. et al. *Neuron* 41, 535-547 (2004)), it is unlikely that in the PSR-morphant brain, alterations of neuron apoptosis results from a shortage of macrophage-derived trophic factors required for the development of target or afferent cells, which normally control neuron apoptosis (see, e.g. Marin-Teva, J. L. et al. *Neuron* 41, 535-547 (2004)). These data suggest that, instead, phagocytic scavengers play a direct role in the progression of the cell death program in neurons.

Failure to complete PCD does not necessarily mean that neurons survive because vertebrates can use alternative cell death pathways (see, e.g. Chautan et al. *Curr. Biol* 9, 967-70 (1999)). To determine whether neurons escape cell death in the absence of macrophage and PSR-signalling, we co-expressed our apoptosis reporter system with a marker of protein synthesis in panther mutants and PSR morphants. This second transgene uses a neuron-specific gene promoter (HuC) to express a short-lived GFP variant which requires constant expression to generate green fluorescence (see, e.g. Li, X., et al. *J. Biol. Chem.* 273, 34970-34975 (1998)). Viable neurons expressing this marker appear green fluorescent but since protein synthesis is rapidly downregulated following caspase-3 activation (see, e.g. Clemens et al. *Cell Death Differ.* 7, 603-615 (2000)), green fluorescence disappears rapidly in apoptotic neurons while fast maturation of stable DsRed.T1 generates red fluorescence (FIG. 3a-b). Consequently, viable neurons are green and apoptotic neurons are red in wild-type transgenics (FIG. 3a, b). In PSR morphants, a third population appears with almost equal green and red fluorescence intensities (FIG. 3 c-h) indicating that in the absence of PSR signalling, neurons which fail to complete the cell death program maintain functional levels of transcriptional activity and protein synthesis. Such neurons can be observed in lower numbers in the panther mutant (FIG. 3h), possibly because non-professional phagocytic scavengers are present in the panther brain but inactivated by PSR deficiency. Surprisingly, these double-labelled neurons remain in the PSR morphant after 4 dpf, when morpholinomodified oligonucleotide efficiency decreases (see, e.g. Nasevicius, A. & Ekker, S. C. *Nat. Genet.* 26, 216-220 (2000)), and for at least 4 days after macrophages finally colonize the brain in panther mutants (FIG. 3h). Detection of red fluorescence at this point doesn't necessarily mean that caspase-3 is still active because DsRed fluorescence can remain stable for days (see, e.g. Bevis et al. *Nat. Biotechnol.* 20, 83-87 (2002); and Verkhusha, V. V., et al. *Biochemisty* 42, 7879-7884 (2003)). However, these results suggest that neurons which escape cell death at one point in development may be unable to die later, even if phagocytic cell clearance is restored. If this is true, the absence of brain macrophages, even during limited periods of development, may have permanent behavioral consequences. Behavioral defects caused by a lack of M-CSF receptor have not been assessed in panther so far, due to a lack of relevant assays in zebrafish. However, M-CSF-deficient mice suffer important cognitive and sensory deficits (see, e.g. Michaelson, M. D., et al. *Development* 122, 2661-2672 (1996); and Pollard, J. W., *Mol. Reprod. Dev.* 46, 54-60 (1997)) suggesting that the control of neuron apoptosis by phagocytic scavengers is critical for normal brain development in vertebrates.

EXAMPLES

Plasmids, Morpholinos and Injections.

G76V mutant zebrafish ubiquitin was generated by PCR using genomic DNA as a template and the following primers: 5'-ATACGAATTCATGCAGATCTTCGTCAAGACC-3' (SEQ ID NO: 3) and 5' GCGGGATCCTGTCGACCAAGCT-TCCCCACCACTCCCCTGAGAC GCAGCAC-3' (SEQ ID NO: 4). The PCR product was cloned into EcoRI-BamHI-digested pDsRed-Express-N1 (Clontech) to generate the control construct UbG-DsRx where UbG76V is fused to DsRed.T1 by a non-cleavable linker. To generate the apoptotic-cell marker UbG-DEVDsRx, DsRed.T1 was PCR amplified using forward primer 5'-GACAGGATCCAGGT-GACGAGGTCGACAAGGGTGACGAGGTC-GACGGTGACG AGGTCGACGGTATGGCCTCCTC-CGAGACG-3' (SEQ ID NO: 5), which introduces 3 DEVD (SEQ ID NO: 1) sites and reverse primer 5'-GAGTCGCG-GCCGCTACAGGAAC AGGTGGTG-3' (SEQ ID NO: 6). The resulting construct was then cloned into BamHI-NotI-digested UbG-DsRx. To generate the double marker UbG-DEVDsRx/HuC-d2EGFP, the entire transcription unit, including the cytomegalovirus promoter, UbG-DEVDsRx and the polyadenylation signal, was PCR amplified using primers 5'-ACTAGTCGACATTAATAG TAATCAAT-TACGGGGTC-3' (SEQ ID NO: 7) and 5'-ATCAGTCGACT-GCCATTCATTACCTCTTTCTCCGCAC-CCGACATAGATACGCC TFAAGATACATTGATGAG-3' (SEQ ID NO: 8) and cloned into XhoI-digested HuCd2EGFP, where 3.5Kb of promoter sequences from the zebrafish pan-neuronal marker HuC have been cloned into a promoterless version of pd2EGFP-N1 (Clontech). Morpholino-modified oligonucleotides were custom-designed by Gene Tools. Sequence of PSR1, which targets the zebrafish PSR gene, was 5'-TTATGGTTCATTCTTCGCCGTIT CG-3' (SEQ ID NO: 9). Sequence of the control (CON) was 5'-CCTCTTACCT-CAGTT ACAATTTATA-3' (SEQ ID NO: 10). Morpholino-modified oligonucleotides were injected in the yolk of one-cell-stage embryos. DNA constructs were linearized and injected in the cytoplasm of one-cell-stage embryos. For each experiment, 200-250 transgenics were generated. Upon reaching the desired age, 20-30 embryos with similar transgene expression levels and low-mosaicism were selected for TUNEL labelling, confocal microscopy, in vivo observations and cell counts.

TUNEL Labelling.

Apoptotic cells with fragmented DNA were labelled using the In Situ Cell Detection Fluorescein Kit (Roche). Selected embryos were fixed for 8 h in 4% paraformaldehyde and rinsed 3 times in PBS before dissection of the yolk and eyes. Tissues were then permeabilized for 15 min in a solution of 5 µg/ml proteinase K solution and post-fixed in 4% paraformaldehyde for 20 min. After three rinses in PBS, tissues were further permeabilized for 15 min in a solution of 0.1% Triton X-100 and 0.1% sodium citrate in PBS. After 3 more rinses, embryos were incubated in a 2% BSA solution in PBS for 1 h to reduce non-specific labelling. TUNEL labelling was then performed for 1 h in the manufacturer's labelling solution followed by 2 final rinses in PBS.

Microscopy and Fluorescence Analysis.

Fixed and live embryos were embedded in 1.2% low-melt agarose on a glass slide and immersed in a drop of water to retain humidity. Whole embryo fluorescence images were collected using an Olympus Optical BX60 microscope equipped with a mercury arc lamp, FITC and rhodamine filters and a Spot digital camera Diagnostic Instruments). Optical sections were obtained using a Leica TCS SP MP fixed-stage upright confocal microscope equipped with argon and krypton lasers. To convert fluorescence intensity to pseudocolors, images obtained by confocal microscopy were imported in a PC version of NIH Image (Scion Image) and converted to black and white 8-bit negatives. Pseudocolors were then obtained using NIH Image inverted rainbow look-up table presented in FIG. 1*j*.

Cell Counts and Statistical Analysis.

To determine percentages of DsRed.T1- and TUNEL-labelled cells, counts were performed on lateral optical sections spanning all main brain regions from the posterior end of the olfactory bulb to the anterior half of the cerebellum. To estimate the percentage of d2EGFP and DsRed.T1-labelled cells in transgenics expressing the UbGDEVDsRx/HuC-d2EGFP double marker, counts were performed in vivo using epifluorescence microscopy. To determine whether cells escaping apoptosis remained d2EGFP-positive even after apoptotic cell clearance was restored, cells were counted on the same batches of live embryos at 24 h intervals for the entire duration of the experiment. For all experiments, 200 cells were counted per fish, 10 fish were used per experiments and all experiments were performed in triplicates. For comparison of two means, paired or unpaired Student t tests were used where appropriate. For multiple comparisons, data were analyzed by one-way analysis of variance.

Throughout this application, various publications are referenced (articles, patents, patent applications etc.). The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A polynucleotide encoding a protease-regulated polypeptide comprising the following operatively linked elements:
   (a) a nucleic acid sequence encoding a protein degradation signal;
   (b) a nucleic acid sequence encoding a polypeptide of interest; and
   (c) a nucleic acid sequence encoding a linker set forth as SEQ ID NO:1 disposed between (a) and (b), wherein the linker comprises a protease recognition motif that is cleaved by a protease;
   wherein, in the presence of the protease, cleavage of the linker protects the polypeptide of interest from proteasomal degradation; and, in the absence of the protease, activity of the polypeptide of interest is decreased.

2. A first vector comprising the polynucleotide of claim 1.

3. A cell comprising the first vector of claim 2.

4. The polynucleotide of claim 1, wherein the protein degradation signal is a ubiquitin degradation signal.

5. The polynucleotide of claim 1, wherein the polypeptide of interest is a reporter protein whose expression can be detected.

6. The polynucleotide of claim 1, wherein the polypeptide of interest is a therapeutically active polypeptide.

7. The first vector of claim 2, further comprising a promoter and/or an enhancer that modulates the expression of the protease-regulated polypeptide.

8. The cell of claim 3, wherein the polypeptide of interest is a first reporter protein, and the cell further comprises a second vector that encodes a second reporter protein whose expression is modulated by a tissue specific promoter or a tissue specific enhancer.

9. A kit comprising the polynucleotide of claim 1 and a suitable container.

* * * * *